United States Patent [19]

Föry et al.

[11] 4,347,372
[45] Aug. 31, 1982

[54] BENZOXAZOLYL-GLYOXYLONITRILE-2-OXIME ETHER DERIVATIVES

[75] Inventors: Werner Föry, of Basel; Haukur Kristinsson, Bottmingen; Henry Szczepanski, Rheinfelden, all of Switzerland

[73] Assignee: Ciba-Geigy Corporation, Ardsley, N.Y.

[21] Appl. No.: 70,288

[22] Filed: Aug. 28, 1979

[30] Foreign Application Priority Data

Sep. 1, 1978 [CH] Switzerland .................. 9255/78

[51] Int. Cl.³ .................. C07D 263/58; A01N 43/76

[52] U.S. Cl. .................. 548/217; 260/465 H; 544/53; 546/329; 544/299; 546/174; 546/336; 546/290; 546/313; 548/136; 546/314; 548/179; 548/255; 548/300; 548/301; 548/544; 549/22; 549/39; 549/74; 549/292; 549/378; 549/398; 549/417; 549/451; 549/491; 549/496; 549/501; 560/132; 560/142; 47/DIG. 3; 71/88; 71/90; 71/92; 71/94; 71/96; 71/105; 71/109; 260/453 RW; 260/465 D; 260/465 F

[58] Field of Search .................. 548/217

[56] References Cited

U.S. PATENT DOCUMENTS 3,927,005 12/1975 Harnisch .................. 548/217

*Primary Examiner*—Anton H. Sutto
*Attorney, Agent, or Firm*—Frederick H. Rabin

[57] ABSTRACT

A process for protecting cultivated plants against aggressive agricultural chemicals is described in which oxime derivatives of the formula

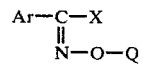

are used as antidotes. Either the cultivated area for the cultivated plants or the cultivated plants themselves or parts of the plant (seeds, tubers, stem parts and the like), as desired, can be treated with these oxime derivatives, which are used as a dressing.

4 Claims, No Drawings

BENZOXAZOLYL-GLYOXYLONITRILE-2-OXIME ETHER DERIVATIVES

The present invention relates to oxime derivatives of the general formula I

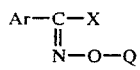

and their preparation and to novel agents based on these compounds and also to the use of such compounds and agents for protecting cultivated plants against aggressive agricultural chemicals.

The active substances have the formula I, in which Ar is a phenyl radical of the formula

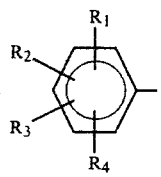

in which $R_1$ is hydrogen, halogen, lower alkyl, $C_1$–$C_{10}$-alkoxy or a phenoxy radical which is in the para-position and is unsubstituted or at most disubstituted by halogen, —CN, $NO_2$ or $CF_3$, $R_2$ is hydrogen, halogen, $NO_2$, lower alkyl, halogenoalkyl or lower alkoxy, $R_3$ is hydrogen or $R_4$ and $R_4$ is phenyl, halogenophenyl, benzyl, halogenobenzyl, cyclohexyl, OH, CN, halogenoalkoxy, lower alkanoyl, lower carbalkoxy, lower alkoxycarbonyl, lower alkoxycarbonyloxy, lower alkylcarbamoyloxy, lower alkylthio, lower alkylsulfonyl, phenalkoxy, $NH_2$, —NH—(lower alkyl), —N(lower alkyl)$_2$, lower alkanoylamino, benzoylamino, carboxamide or sulfonamide, or Ar is also a 5-membered to 10-membered heterocyclic radical which contains not more than three identical or different hetero-atoms N, O and/or S and which can be bonded via a $C_1$- to $C_3$-aliphatic chain to the remainder of the molecule and which is substituted by $R_1$, $R_2$ or $R_3$ and can be substituted by oxo or thiono, with the proviso that, if Q is not H and a furan or thiophen ring is present, the latter carries at least one substituent other than hydrogen and that, in the case of a furan or thiophen ring which is monosubstituted or disubstituted by halogen, nitro or lower alkyl, this ring is substituted by a third substituent other than hydrogen, X is hydrogen, CN, halogen, $C_1$–$C_{10}$-alkyl, lower alkanoyl, —COOH, a carboxylic acid ester or a carboxamide radical and Q is hydrogen, lower alkyl, which can be interrupted by hetero-atoms or substituted by halogen or cyano, lower alkenyl or halogenoalkenyl, lower alkynyl, $C_3$–$C_7$ cycloalkyl, which is unsubstituted or substituted by halogen, or a lower alkanecarboxylic acid ester group, a lower alkanecarboxylic acid thioester group, a lower alkanecarboxamide group, an aliphatic acyl radical, an araliphatic, cycloaliphatic or substituted or unsubstituted aromatic or heterocyclic acyl radical, an alkylsulfonyl radical, a sulfonamide radical, a metal salt, a quaternised ammonium salt or an aliphatic, araliphatic, cycloaliphatic or substituted or unsubstituted aromatic or heterocyclic carbonic acid, thiocarbonic acid or carbamoyl radical.

In the formula I, halogen is to be understood as meaning fluorine, chlorine, bromine or iodine.

Carboxylic acid esters and carboxylic acid thioesters are carboxylic acid lower alkyl esters and carboxylic acid lower alkyl thioesters. Acyl radicals are to be understood as meaning carboxylic acid radicals. In addition to —$CONH_2$ and —$SO_2$—$NH_2$, carboxamides and sulfonamides are also monoalkyl-substituted or symmetrically or asymmetrically dialkyl-substituted or N-alkyl-N-alkoxy-substituted amides, in which the alkyl groups are lower alkyl.

The term alkyl, on its own or as part of a substituent, comprises branched or unbranched $C_1$- to $CH_{10}$-alkyl groups; lower alkyl, on its own or as part of a substituent, is $C_1$–$C_4$ alkyl. Examples are methyl, ethyl, propyl, isopropyl, butyl, isobutyl, sec.-butyl and tert.-butyl and also the higher homologues amyl, isoamyl, hexyl, heptyl, octyl, nonyl and decyl, including the isomers thereof. Accordingly, alkanoyls or cyanoalkyls contain an additional C atom. Correspondingly, lower alkenyl or alkynyl groups contain not more than 4 C atoms.

The term aliphatic group includes both saturated (alkyls) and unsaturated (alkenyls, alkadienyls and alkynyls), halogen-substituted and cyano-substituted radicals, and radicals interrupted by oxygen, which contain not more than 10 carbon atoms.

The term aromatic group comprises phenyl and naphthyl.

An araliphatic radical comprises a phenyl or naphthyl which is unsubstituted or monosubstituted to trisubstituted and is bonded via lower alkyl or lower alkenyl to the remainder of the molecule. Examples are the parent structures benzyl, phenethyl, phenylallyl and homologues.

The term heterocyclic acyl radical comprises 5-membered or 6-membered heterocyclic carboxy compounds with a ring hetero-atom from the series comprising N, O or S. Examples are the radicals of furancarboxylic acid, thiophencarboxylic acid, nicotinic acid, isonicotinic acid and others.

A 5-membered to 10-membered heterocyclic radical Ar can be monocyclic or bicyclic.

Examples from the series of monocyclic rings are pyrrole, thiophen, furan, imidazole, pyrazole, oxazole, thiazole, thiadiazole, triazole, pyridine, pyrazine, pyrimidine, pyridazine and triazines and also their partially or completely hydrogenated derivatives; further radicals of this series are azetidine, aziridine, morpholine, thiomorpholine, oxathiine, dioxan, dioxolane, dithiolane, dithiane and others.

Radicals of the bicyclic series of 5-membered to 10-membered heterocyclic structures are the ring systems listed above in combination with a fused benzene ring (for example benzofuran, indole, benzodioxolane, benzthiazole, benzoxazole, quinoline, benzothiadiazine, benzotriazine and others) and also those containing heteroatoms in both rings (for example quinolizidine, purine and the like).

Further heterocyclic ring systems are formed by the incorporation of oxo and/or thiono, for example hydantoin, thiohydantoin, triazinone, coumarin, pyrone, maleic acid hydrazide, maleic anhydride, glutaric anhydride, barbituric acid and others.

N-Heterocyclic structures also include N-oxides.

Cycloalkyl groups are cyclopropyl, cyclobutyl, cyclopentyl, cyclohexyl and cycloheptyl. Cycloaliphatic radicals correspond to these ring systems but, in addition, can also contain one or several double bonds, depending on what is possible.

Metal salts are to be understood as meaning cations of groups I to IV of the periodic table and also heavy metal salts. Examples are Na, K, Ca, Mg, Al, Zn, Cu, Fe, Mn, Co and Ni.

Quaternary ammonium salts contain, as identical or different substituents, hydrogen, $C_1$-$C_{12}$ alkyl, lower hydroxyalkyl, benzyl, amino and di-lower alkylamino, or form, from two valencies and the N atom, a 5-membered or 6-membered heterocyclic ring which can contain a further hetero-atom N, O or S.

Oximes of the formula I are outstandingly suitable for protecting cultivated plants such as rice, maize and species of cereal (cultivated millet, wheat, rye, barley and oats) against attack by agricultural chemicals which are aggressive to plants, especially by herbicides belonging to very diverse categories of substances, if these do not act selectively or do not act sufficiently selectively, i.e. damage not only the weeds to be combated but also the cultivated plants to a greater or lesser extent.

Diverse substances which are capable of specifically antagonising the harmful action of a herbicide on the cultivated plants, i.e. of protecting the cultivated plant without noticeably influencing the herbicidal action on the weeds to be combated, have already been proposed as antidotes. Depending on its characteristics, an antidote of this type, which is also termed a safener, can be used for the pretreatment of the seed of the cultivated plant (dressing of the seed or of the cuttings) or before sowing, in the seed furrows, or as a tank mixture, on its own or together with the herbicide, before or after emergence of the plants.

Thus, British Pat. No. 1,277,557 describes the treatment of seeds and seedlings of wheat and sorghum with certain oxamic acid esters and amides before attack by N-methoxymethyl-2',6'-diethyl-chloroacetanilide (Alachlor). Other literature sources (German Offenlegungsschrift No. 1,952,910, German Offenlegungsschrift 2,245,471 and French Pat. No. 2,021,611) propose antidotes for the treatment of cereals, maize seed and rice seed in order to protect them against attack by herbicidal thiolcarbamates. In German Pat. No. 1,576,676 and U.S. Pat. No. 3,131,509, hydroxy-amino-acetanilides and hydantoins are proposed for the protection of cereal seeds against carbamates such as IPC, CIPC and the like. However, on further development all of these preparations have proved inadequate.

Preferred antidotes are those compounds of the formula I in which Ar is a substituted or unsubstituted pyridine radical, a substituted or unsubstituted thiophen radical, a substituted or unsubstituted benzoxazole, benzthiazole or benzimidazole radical, a substituted or unsubstituted thiadiazole radical or a substituted or unsubstituted imidazole, imidazoline or imidazolidine radical.

A preferred group of compounds comprises those of the formula

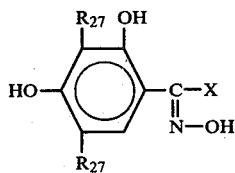

in which X is as defined under formula I and $R_{27}$ is a halogen atom, preferably chlorine or bromine, and in which the three hydroxyl groups are in the free form or in the form of $NH_4^+$ or of metal salts or are partially or completely carbamoylated and/or etherified by lower aliphatic groups. Important carbamate groupings on one, two or all three of the hydroxyl groups are those which are formed by reaction of a $C_1$-$C_6$ alkyl isocyanate or of a phenyl isocyanate which is unsubstituted or substituted by halogen or lower alkyl. A particularly preferred antidote is the compound of the formula

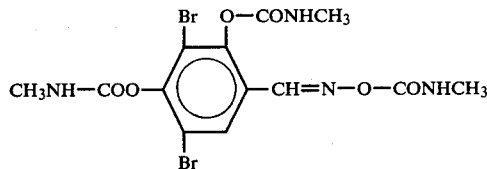

which is listed under No. 198 in this specification, and also further compounds of this type in which X is not hydrogen and which contain three lower alkylcarbamoyloxy groups of an analogous type.

Another preferred group of compounds comprises those of the formula

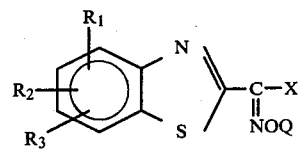

in which X is CN or a carboxylic acid ester, Q is lower alkyl, which can be interrupted by hetero-atoms or substituted by halogen or cyano, lower alkenyl or halogenoalkenyl, lower alkynyl, an aliphatic, araliphatic, cycloaliphatic or substituted or unsubstituted aromatic or heterocyclic acyl radical, an alkylsulfonyl radical or an aliphatic, araliphatic, cycloaliphatic or substituted or unsubstituted aromatic or heterocyclic carbamoyl radical and $R_1$, $R_2$ and $R_3$ are as defined for formula I. Especially preferred are those in which $R_1$, $R_2$ and $R_3$ are hydrogen.

Another preferred group of compounds comprises those of the formula

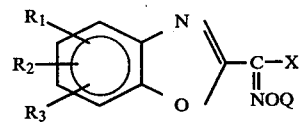

in which X is methyl, CN or a carboxylic acid ester, Q is lower alkyl, which can be interrupted by hetero-atoms or substituted by halogen or cyano, lower alkenyl or halogenoalkenyl, lower alkynyl, an aliphatic, araliphatic, cycloaliphatic or substituted or unsubstituted aromatic or heterocyclic acyl radical, an alkylsulfonyl radical or an aliphatic, araliphatic, cycloaliphatic or substituted or unsubstituted aromatic or heterocyclic carbamoyl radical and $R_1$, $R_2$ and $R_3$ are as defined for formula I. Especially preferred are those in which $R_1$, $R_2$ and $R_3$ are hydrogen.

Another preferred group of compounds comprises those of the formula I wherein Ar is the group

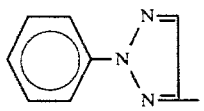

X is hydrogen or Q is hydrogen or an aliphatic carbamoyl radical.

Another preferred group of compounds comprises those of the formula I wherein Ar is the group

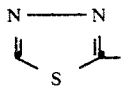

which is substituted by lower alkoxy, lower alkylthio, lower alkylsulfinyl, lower alkylsulfonyl or phenyl, Q is hydrogen, lower alkyl, which can be interrupted by heteroatoms or substituted by halogen or cyano, or an aliphatic acyl radical, and X is as defined for formula I. Especially preferred are those wherein X is CN, halogen or carboxylic ester.

Another preferred group of compounds comprises those of the formula I, wherein Ar is the group

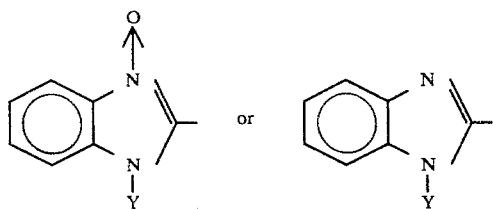

which can be substituted by halogen and in which Y is lower alkyl, lower alkoxycarbonyl or phenyl, Q is hydrogen or an aliphatic, araliphatic, cycloaliphatic or substituted or unsubstituted aromatic or heterocyclic acyl or carbamoyl radical, and X is as defined for formula I.

Another preferred group of compounds comprises those of the formula I, wherein Ar is the group

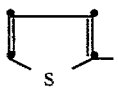

which can be monosubstituted or disubstituted by halogen, Q is hydrogen, and X is as defined for formula I.

Another preferred group of compounds comprises those of the formula I, wherein Ar is the group

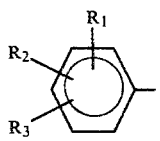

in which $R_1$ is hydrogen, halogen or lower alkyl, $R_2$ is hydrogen, halogen, lower alkyl or halogenalkyl and $R_3$ is lower alkoxycarbonyloxy, lower alkylcarbamoyloxy or lower carbalkoxy and X is $C_1$–$C_{10}$-alkyl, CN or carboxylic acid ester, and Q is as defined in formula I.

Another preferred group of compounds comprises those of the formula I, wherein Ar is the group

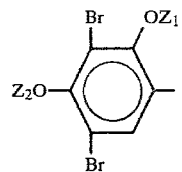

in which $Z_1$ and $Z_2$ independently of one another are lower alkylcarbamoyl, cycloalkylcarbamoyl, arylcarbamoyl, lower alkyl, lower alkenyl, lower alkynyl or lower halogenoalkyl, X is hydrogen, and Q is hydrogen, $NH_4^+$, metal salt, lower alkylcarbamoyl, cycloalkylcarbamoyl, arylcarbamoyl or a lower aliphatic residue.

Surprisingly, oximes of the formula I have the property of protecting cultivated plants against the attack of agricultural chemicals which are aggressive to plants, especially against herbicides of very diverse categories of substances, including 1,3,5-triazines, 1,2,4-triazinones, phenylurea derivatives, carbamates, thiolcarbamates, phenoxyacetic acid esters, phenoxypropionic acid esters, halogenoacetanilides, halogenophenoxyacetic acid esters, substituted phenoxyphenoxy-acetic acid esters and -propionic acid esters, substituted pyridinoxyphenoxy-acetic acid esters and -propionic acid esters, benzoic acid derivatives and the like, if these are not tolerated or are not adequately tolerated by the cultivated plants.

Depending on the intended application, an antidote, of this type, of the formula I can be employed for the pre-treatment of the seed of the cultivated plant (dressing of the seed or of the cuttings) or can be added to the soil before or after sowing or can be applied, on its own or together with the herbicide, before or after emergence of the plants. In principle, therefore, the treatment of the plant or of the seed with the antidote can be effected independently of the time at which the phytotoxic chemicals are applied. It can, however, also be carried out at the same time (tank mixture). Pre-emergence treatment includes both treatment of the cultivated area before sowing (ppi="pre plant incorporation") and treatment of the cultivated areas after sowing but before emergence of the plants.

The amounts of antidote applied, relative to the herbicide, largely depend on the type of application. If a field treatment is carried out, the ratio of the amount of antidote of the formula I to the amount of phytotoxic chemical is 1:100 to 5:1 and preferably 1:20 to 1:1. In the case of seed dressing and similar controlled protective measures, however, much smaller amounts of antidote are required relative to the amounts of herbicide which, for example, are subsequently used per hectare of cultivated area (for example about 1:3,000 to 1:1,000). As a rule, there is only a loose relationship between protective measures, such as seed dressing with an antidote of the formula I, and possible subsequent field treatment with agricultural chemicals. Pre-treated seed and plants can subsequently come into contact with diverse chemicals in agriculture, horticulture and forestry.

The invention relates not only to agents which contain these oxime ethers of the formula I together with herbicides but also to agents which contain these oxime ethers of the formula I as the sole active component. It is possible to prepare, market or use plant protection agents which contain an antidote of the formula I (also termed a safener), without the herbicide which is to be weakened (or another aggressive agricultural chemical)

being present at the same time. One important application possibility is seed dressing, which is carried out at a time which is entirely independent of the use of the agricultural chemical (for example herbicide). Another field of application is the treatment of a soil which still contains residual amounts of a herbicide from the previous cultivation season, which could damage the intended new plant crop.

The antidote characteristic is a substance characteristic which is independent of the cultivated plant and of the agricultural chemical which has the action which is to be selectively weakened and is a characteristic which is inherent to a preparation of the formula I but becomes evident only on interaction of the 3 components antidote/agricultural chemical/plant. Just as the pesticidal action of a chemical which acts as a pesticide is evident only when a pest is present, the detection of the safener action also demands the presence of the other two components which participate in the action, i.e. the agricultural chemical (for example the herbicide) and the cultivated plant. This differentiates a formulated safener agent from a two- or three-component mixture having a synergistic action, in which all the active components are present at the same time and all have an action directed towards the same goal.

Within the framework of the present invention, cultivated plants are all plants which yield produce in any form (seeds, roots, stems, tubers, leaves, blossom and constituents such as oils, sugar, starch, protein and the like) and are cultivated and tended for this purpose. These plants include, for example, all species of cereals, maize, rice, millet, soya, beans, peas, potatoes, vegetables, cotton, sugar beet, cane sugar, peanuts, tobacco and hops but also decorative plants, fruit trees and banana, cacao and natural rubber plants. This list imposes no limitations. In principle, an antidote can be employed wherever a cultivated plant is to be protected against the phytotoxicity of a chemical.

The invention also relates to a process for protecting cultivated plants against aggressive (phytotoxic) agricultural chemicals, by applying an oxime derivative of the formula I, which acts as an antidote, before or after application of the agricultural chemical or at the same time as the agricultural chemical, as desired.

The invention also relates to the propagation material of such cultivated plants, which has been treated protectively with an oxime derivative of the formula I. The term "propagation material" is to be understood as meaning all generative parts of plants which can be used for propagation of the cultivated plant. These include seed grains (seed in the narrower sense), roots, fruit, tubers, rhizomes, stem parts, branches (cuttings) and other parts of plants. However, they also include germinated plants and young plants which are to be further transplanted after germination or emergence. Young plants of this type can be protected in a controlled manner by a complete or partial immersion treatment before further transplanting.

The free oximes which fall within the scope of the formula I can be prepared by methods known per se for converting compounds of the formula II

  Ar—CH$_2$—X  (II)

(in which the symbols are as defined under formula I) to the oxime by reaction with nitrous acid (HNO$_2$) or an organic or inorganic nitrite. They can also (depending on the substituent X) be obtained from keto compounds of the formula III

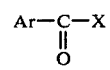

$$Ar-\underset{\underset{O}{\|}}{C}-X \qquad (III)$$

by reaction with hydroxylamine.

The free oximes obtained in this way can then, if desired, be converted to the other derivatives which are included under the formula I and specifically can, as desired, (a) be converted to the salts using bases or (b) be acylated with acids or acid halides or (c) be converted to oxime carbamates using isocyanates or carbamoyl halides or (d) be converted to (thiolo)carbonates using halogenocarbonic acid (thio)esters or (e) be converted to other oxime ethers listed under Q using radicals which detach halogen or (f) be converted by means of COCl$_2$ to chlorides, which form carbamates with amines.

If the reactant carries a radical which detaches halogen, the free oxime is preferably employed in the form of a salt, preferably an alkali metal salt.

With reference to the methods of preparation, the following literature may be cited: German Offenlegungsschrift 2,312,956; German Offenlegungsschrift 2,350,910; "Berichte der deutschen Chem. Gesellschaft" 42, page 738 et seq. [1909]; J. F. prakt. Chemie 66, page 353; Liebigs Ann. 250, 165 and Organic Reactions 1953, Volume 7, page 343 and 373.

Solvents suitable for use in obtaining the compounds of the formula I are, in principle, all solvents which are inert under the reaction conditions. Examples are hydrocarbons, but in particular polar solvents, such as acetonitrile, dioxan, Cellosolve, dimethylformamide, anhydrous acetic acid, pyridine and the like.

The temperatures are in the range of $-20°$ to about $150°$ and preferably between $20°$ and $60°$.

Substances which can be employed as the agents which detach hydrogen halide are bases such as tertiary amines (triethylamine, triethylenediamine, N-methylpiperidine, N-methylmorpholine and dimethylaniline). In some cases, a suspension of anhydrous Na$_2$CO$_3$ or anhydrous K$_2$CO$_3$ in the anhydrous reaction medium or of NaOH solutions under phase transfer conditions suffices for this purpose.

Oximes exist in two stereoisomeric forms, the syn-form and the anti-form. All of the said end products have the formula I and can exist in the two forms, as the pure compound or as mixtures. Within the scope of the present description, accordingly, the compounds are to be understood as meaning the two stereoisomeric forms, on their own and as mixtures in any desired reciprocal mixing ratio.

The following examples illustrate the preparation of oxime derivatives of the formula I. The temperatures in the examples and in the following table are in degrees centigrade.

EXAMPLE 1

Preparation of the compound

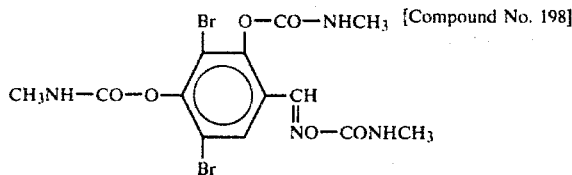

2,4-Dihydroxy-3,5-dibromo-benzaldoxime tris-(methylcarbamate)

6 g of 3,5-dibromo-2,4-dihydroxy-benzaldoxime were dissolved in 50 ml of dimethylsulfoxide and a little diazabicyclooctane was added. 4 ml of methyl isocyanate were now added with cooling (<20° C.) and stirring and the mixture was then stirred thoroughly at room temperature for 12 hours. The reaction mixture was poured into ice-water and salted out. The suspension was filtered with suction, the residue was washed with water and dissolved in a little dimethylformamide and active charcoal was added to the solution.

This solution was filtered with suction and the end product was precipitated by adding water to the filtrate: 9 g of compound 198, melting point 131°–133° C.

EXAMPLE 2

Preparation of

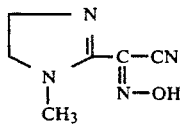

α-(1-Methyl-imidazolin-2-yl)-α-oximino-acetonitrile 12.3 g (0.1 mol) of 1-methyl-2-cyanomethyl-2-imidazoline are initially introduced into 50 ml of glacial acetic acid. A solution of 7.8 g (0.1 mol) of $NaNO_2$ in 20 ml of water is added dropwise at about 15°, with cooling. The mixture is stirred for 2 hours, cooled and filtered and the residue is washed with a little cold water. This yields 11 g (=73% of theory) of end product, which is recrystallised from methanol; melting point 216.5° C.

EXAMPLE 3

Preparation of

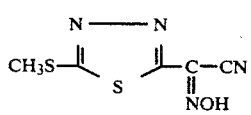

α-[5-Methylthio-1,3,4-thiadiazol-2-yl]-α-oximino-acetonitrile 17.1 g (0.1 mol) of 2-cyanomethyl-5-methylthio-1,3,4-thiadiazole are intially introduced into 75 ml of glacial acetic acid. A solution of 7.8 g (0.11 mol) of $NaNO_2$ in 20 ml of water is added dropwise and the mixture is stirred for 1 hour. 200 ml of water are then added to the solution and the mixture is filtered. The residue is washed with water: 19 g (95% of theory) of end product, melting point >200° C. (decomposition).

EXAMPLE 4

Preparation of

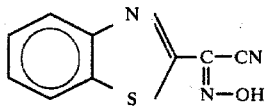

α-[Benzthiazol-2-yl]-α-oximino-acetonitrile

A solution of 7.8 g (0.1 mol) of $NaNO_2$ in 20 ml of water is added dropwise at room temperature to 17.4 g (0.1 mol) of 2-cyanomethyl-benzthiazole in 50 ml of glacial acetic acid. The end product is filtered off after 2 hours and washed with water: 19.5 g (96% of theory), melting point >170° (decomposition).

EXAMPLE 5

Preparation of

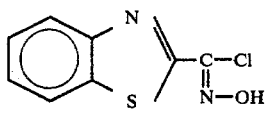

Benzthiazol-2-yl-hydroxamic acid chloride 36.7 g (0.2 mol) of 2-chloromethylbenzthiazole and 23.4 g (0.2 mol) of isopentyl nitrite are initially introduced into 200 ml of dioxan. About 0.4 mol of hydrogen chloride gas is passed in over a period of 30 minutes, with cooling (<50° C.). After stirring for 2 hours, the mixture is cooled and the end product is filtered off and washed with a little dioxan and then with petroleum ether: 39.5 g (93% of theory), melting point 192°.

EXAMPLE 6

Preparation of

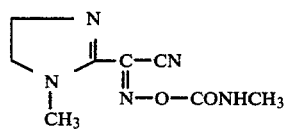

α-[1-Methyl-imidazolin-2-yl]-α-(O-methylaminocarbonyl-oximino)-acetonitrile 15.2 g (0.1 mol) of α-[1-methyl-imidazolin-2-yl]-α-oximino-acetonitrile and 6.4 g (0.11 mol) of methyl isocyanate are stirred in 200 ml of ethyl acetate with a few drops of triethylamine for 16 hours. 16 g (76.5% of theory) of end product are filtered off and this is washed with a little ethyl acetate; melting point 186°–190° C. (decomposition).

EXAMPLE 7

Preparation of

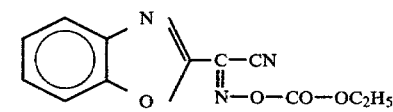

α-[Benzoxazol-2-yl]-α-[O-ethoxycarbonyl-oximino]-acetonitrile 12 g (0.11 mol) of ethyl chloroformate are added dropwise to a solution of 18.7 g (0.1 mol) of α-[benzoxazol-2-yl]-α-oximino-acetonitrile in 120 ml of pyridine, with ice-cooling. After stirring for 3 hours, the mixture is poured into 1 liter of ice-water and the residue is filtered off and washed with water: 23 g (89% of theory) of end product, which is recrystallised from acetonitrile; melting point 187° C.

EXAMPLE 8

Preparation of

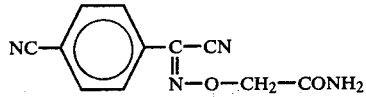 [Compound 25]

9.7 g (0.05 mol) of the Na salt of α-oximino-α-(4-cyanophenyl)-acetonitrile, 9.3 g (0.05 mol) of iodoacetamide and 50 ml of acetonitrile are added together and the mixture is stirred for 3 hours at 50°–60° and cooled to room temperature, whereupon the end product starts to precipitate out. The suspension is poured into ice-water and the residue is filtered off with suction and washed with water and hexane: 9.2 g (80.7% of theory), melting point 197°–199° C.

EXAMPLE 9

Preparation of

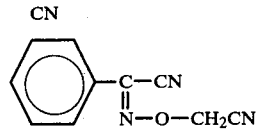 [Compound 29a]

m-Cyanophenylglyoxylonitrile-2-oxime cyanomethyl ether 9.6 g (0.05 mol) of the Na salt of α-(3-cyanophenyl)-α-oximino-acetonitrile and 11.3 g (0.15 mol) of chloroacetonitrile are heated in 50 ml of acetonitrile for 3 hours at 50°–60°, with stirring. The suspension, which has become dark, is evaporated and water is added to the residue. The desired end product is extracted from this mixture with methylene chloride and this extract, after drying over Na sulfate and stirring with active charcoal, is filtered to give a clear filtrate. The filtrate is evaporated: 7.7 g of end product, melting point 93° C.

Compounds which can be prepared in this way or by one of the methods indicated above are the following compounds of the formula

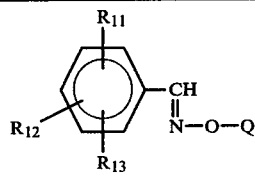

| Compound No. | $R_{11}$ | $R_{12}$ | $R_{13}$ | Q | Melting point |
|---|---|---|---|---|---|
| 1 | 2-OH | 3-Cl | 5-Cl | H | 193–197° |
| 2 | 4-OH | 3-Cl | 5-Cl | H | 178–181° |
| 3 | 2-OH | 4-Cl | H | H | 123–124° |
| 4 | 2-OH | 4-Br | H | H | 126–127° |
| 5 | 2-OH | 4-CH$_3$ | 6-CH$_3$ | H | 126.4–127° |
| 6 | 3-OH | H | H | H | 90–92° |
| 7 | 4-OH | H | H | H | 95–99° |
| 8 | 2-OH | H | H | H | 57–59° |
| 8a | 4-O—CONHCH$_3$ | H | H | —CONHCH$_3$ | |
| 9 | 4-O—CONHCH$_3$ | 2-CH$_3$ | H | H | 142–143° |
| 10 | 4-OH | 2-CH$_3$ | 6-C$_2$H$_5$ | H | 142–146° |
| 11 | 2-OCONHCH$_3$ | H | H | H | 133–135° (decomposition) |
| 12 | 4-OCOCH$_3$ | 2-NO$_2$ | 3-OCH$_3$ | H | 155–158° |
| 13 | 2-CONHCH$_3$ | H | H | —CONHCH$_3$ | 126–129° |
| 14 | 4-OH | 3-Br | 5-Br | —COC$_2$H$_5$ | 132–133° |
| 15 | 4-N(C$_2$H$_5$)$_2$ | H | H | H | 93–96° |
| 16 | 2-OCONH—C$_6$H$_5$ | H | H | —CONH—C$_6$H$_5$ | 233° |
| 17 | 2-OH | 3-CH$_3$ | 5-C$_4$H$_9$(t) | H | 109° |
| 18 | 4-OH | 3-OCH$_3$ | H | 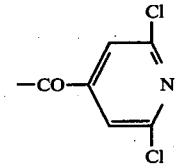 | 117–118° |
| 19 | 2-NH—COC$_6$H$_5$ | H | H | H | 157–159° |
| 20 | 2-O—CONHCH$_3$ | H | H | H | 159° (decomposition) |
| 21 | 2-O—COCH$_3$ | 3-Cl | 5-Cl | —COCH$_3$ | 114–116° |
| 22 | 4-OH | 3-Cl | 5-Cl | —CONHCH$_3$ | 160–162° |
| 23 | 2-O—CONHCH$_3$ | 4-CH$_3$ | 6-CH$_3$ | —CONHCH$_3$ | 130–135° | and also the following compounds of the formula

-continued

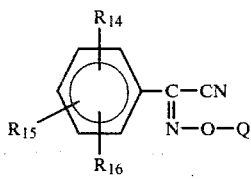

| Compound No. | $R_{14}$ | $R_{15}$ | $R_{16}$ | Q | Physical constant |
|---|---|---|---|---|---|
| 24 | 4-CN | H | H | —COC$_6$H$_5$ | m.p. 147–150° |
| 25 | 4-CN | H | H | —CH$_2$CONH$_2$ | m.p. 197–199° |
| 26 | 4-CN | H | H | —CH$_2$CN | m.p. 133–136° |
| 27 | 4-CN | H | H | —nC$_3$H$_7$ | $n_D^{20}$1.5609 |
| 28 | 4-SO$_2$NH$_2$ | H | H | H | m.p. 236° |
| 29 | 4-OCF$_2$CHFCl | H | H | —CH$_2$CN | oil |
| 29a | 3-CN | H | H | —CH$_2$CN | m.p. 93° | and also the following compounds of the formula

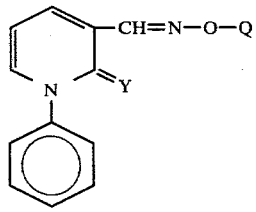

| Compound No. | Y | Q | Melting point |
|---|---|---|---|
| 30 | S | H | 167–168° |
| 31 | S | —CH(CH$_3$)COOCH$_3$ | 122–126° |
| 32 | O | H | 218–219° |
| 33 | S | —CONHC$_4$H$_9$(tert.) | 192–202° |
| 34 | O | —CH$_2$CN | 167–168° |
| 35 | S | —CH$_2$—COOCH$_3$ | 173–174° |
| 36 | O | —CH(CH$_3$)COOCH$_3$ | 129–131° | and also the following compounds of the formula

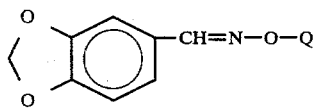

| Compound No. | Q | Physical constant |
|---|---|---|
| 37 | —CH$_2$—C≡CH | melting point 56–58° |
| 38 | —CH$_2$—CN | oil |
| 39 | —CH$_2$—CO—NH$_2$ | oil |
| 40 | —CH$_2$—C≡C—CH$_3$ | oil |
| 41 | —CH$_2$—CH=CH$_2$ | oil |
| 42 | —CH$_2$—C(Cl)=CCl$_2$ | oil |
| 43 | —CH$_2$—COOCH$_3$ | oil |
| 44 | —CH$_2$—CH=C(CH$_3$)—C$_2$H$_5$ | $n_D^{20}$1.5604 |
| 45 | —CO—NH—CH$_3$ | oil |
| 46 | —CO—N(CH$_3$)$_2$ | oil | and also the following compounds of the formula

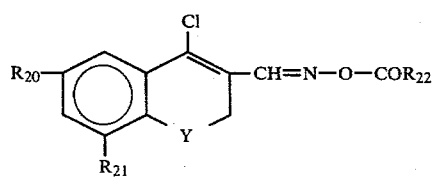

| Compound No. | Y | $R_{21}$ | $R_{20}$ | $R_{22}$ | Melting point |
|---|---|---|---|---|---|
| 47 | O | H | Cl | —OCH$_3$ | 155° |

-continued

| | | | | | |
|---|---|---|---|---|---|
| 48 | O | H | Cl | —NHCH$_3$ | 156° |
| 49 | O | Cl | H | —NHCH$_3$ | 211° |
| 50 | O | Cl | Cl | —OCH$_3$ | 182° |
| 51 | O | Cl | Cl | —NHCH$_3$ | 224° |
| 52 | O | Cl | H | —OCH$_3$ | 132° |
| 53 | S | H | Cl | —NHCH$_3$ | 186° |
| 54 | S | Cl | Cl | —NHCH$_3$ | 212° | and also the following compounds of the formula

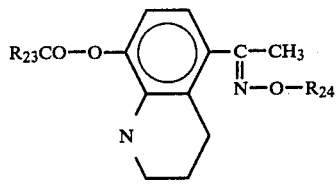

| Compound No. | R$_{23}$ | R$_{24}$ | Melting point |
|---|---|---|---|
| 55 | —OC$_2$H$_5$ | —COOC$_2$H$_5$ | 99° |
| 56 | —OC$_3$H$_7$(iso) | —COOC$_3$H$_7$(iso) | 103° |
| 57 | CH$_3$ | —CO—CH$_3$ | 127° |
| 58 | CH$_3$ | —CO—NHCH$_3$ | 169° |
| 59 | —NHC$_2$H$_5$ | —CO—NHC$_2$H$_5$ | 152° |
| 60 | —NHC$_3$H$_7$(iso) | —CO—NHC$_3$H$_7$(iso) | 135° |
| 61 | —NHC$_3$H$_7$(n) | —CO—NHC$_3$H$_7$(n) | 142° |
| 62 | —NHC$_4$H$_9$(n) | —CO—NHC$_4$H$_9$(n) | 138° |
| 63 | —NHCH$_3$ | —CO—NHCH$_3$ | 141° |
| 64 | —NH—C$_6$H$_5$ | —CO—NH—C$_6$H$_5$ | 129° |
| 65 | —NH—CH$_3$ | H | 144° | and also the following compounds of the formula

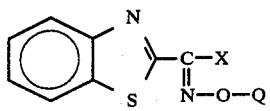

| Compound No. | X | Q | Melting point |
|---|---|---|---|
| 66 | —CN | H | 170° (decomposition) |
| 67 | CN | Na$^+$ | (solid) |
| 68 | CN | —CON(CH$_3$)$_2$ | 200° |
| 69 | CN | —COCH$_3$ | 168° |
| 70 | CN | —CO—OC$_3$H$_7$(iso) | 186° |
| 71 | CN | —SO$_2$—CH$_3$ | 202° |
| 72 | CN | —CO—NHCH$_3$ | 164° |
| 73 | CN | —CO—CH=CH—CH$_3$ | 75° |
| 74 | CN | CH$_3$ | 152° |
| 75 | CN | —CH$_2$—C≡CH | 118° |
| 76 | —COOC$_2$H$_5$ | H | 120° (decomposition) |
| 77 | —CN | —CH$_2$—CN | 207° |
| 78 | CN | —CONH—C$_6$H$_4$—Cl(4) | 194° |
| 79 | CN | —CO—C$_6$H$_3$Cl$_2$(2,4) | 190° (decomposition) |
| 80 | CN | —CONH—C$_6$H$_3$Cl(3)-CF$_3$(4) | 206° |
| 81 | CN | —CO—C$_6$H$_4$Cl(4) | 190° |
| 82 | Cl | H | 192° |
| 83 | Cl | —CONHCH$_3$ | |
| 84 | Cl | —CONH—C$_6$H$_5$ | |
| 85 | COOCH$_3$ | H | 124° (decomposition) |
| 86 | CN | —CONH—CH$_2$—CH=CH$_2$ | 130° |
| 87 | CN | —S—CH$_2$—CH=CH$_2$ | 117° |
| 87a | CN | —SO$_2$—C$_6$H$_5$ | 204° | and also the following compounds of the formula

-continued

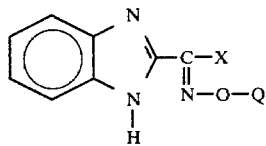

| Compound No. | X | Q | Melting point |
|---|---|---|---|
| 88 | CN | H | >270° (decomposition) |
| 89 | CN | Na+ | (solid) |
| 90 | CN | —CON(CH3)2 | >240° (decomposition) |
| 91 | CN | —SO2CH3 | >210° (decomposition) |
| 92 | CN | —CONHCH3 | >210° (decomposition) |
| 93 | CN | —COCH3 | 210° |
| 94 | CN | —CH2—CN | 179° |
| 95 | CN | —CO—NHC2H5 | 285° |
| 96 | CN | —CO—NHC3H7(n) | 233° |
| 97 | CN | —CO—NHC3H7(iso) | 112° (decomposition) |
| 98 | CN | —CO—NHC4H9(n) | 238° (decomposition) |
| 99 | CN | —CO—NHC4H9(tert.) | 310° (decomposition) |
| 100 | CN | —CO—C6H3Cl2(3,4) | >250° (decomposition) |
| 101 | CN | —CO—NHC6H4Cl(4) | >200° (decomposition) |
| 102 | Cl | —CH2CN | |
| 103 | Cl | —CH2—C≡CH | |
| 104 | Cl | —CH2—CH=CH2 | |
| 105 | Cl | —CH2—CH=CH—CH3 | |
| 106 | CN | —CH2—CH=CH—CH3 | |
| 107 | CH3 | —CH2—CH=CH—CH3 | |
| 108 | CN | —CH2—CONH2 | | and also the following compounds of the formula

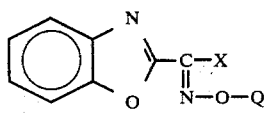

| Compound No. | X | Q | Melting point |
|---|---|---|---|
| 109 | CN | H | 220° (decomposition) |
| 110 | CN | —CO—CH3 | 180° |
| 110a | CN | —CO—CH2Cl | |
| 111 | CN | —CO—OC2H5 | 199° |
| 112 | CN | —CON(CH3)2 | 212° |
| 113 | CN | —CO—NHCH3 | >170° (decomposition) |
| 114 | CN | —SO2CH3 | 207° |
| 115 | CN | —CH2—C≡CH | 107° |
| 116 | —COOC2H5 | H | 134° (decomposition) |
| 117 | —COOCH3 | H | 137° (decomposition) |
| 118 | CN | CH3 | 125° |
| 119 | CN | —CO—OC3H7(iso) | 179° |
| 120 | CN | —CO—C4H9(n) | (solid) |
| 121 | CN | —CO—N(CH3)—OCH3 | 171° |
| 122 | CN | —CO—OCH3 | 173° |
| 123 | CN | —COC3H7(n) | 96° |
| 124 | CN | —CO—CH=CH—CH3 | 153° |
| 124a | CN | —CO—CH=CH2 | |
| 125 | CN | —CO—SC2H5 | 154° |
| 126 | CN | —CO—NH—CH2CH2Cl | 150–155° |
| 127 | CN | —NH—CH2Cl | 165–168° |
| 128 | CN | —CH2—CN | 164° |
| 129 | CN | 2-Furanoyl | 230° |
| 130 | CN | —CO—C6H3Cl2(3,4) | >210° (decomposition) |
| 131 | CN | —CO—NH—C6H3Cl2(3,5) | 197° |
| 132 | CN | —CO—C6H4Cl(2) | 145° |

-continued

| | | | |
|---|---|---|---|
| 133 | CN | 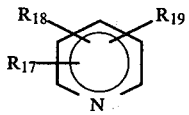—CO—C₆H₃(CH₃)(NO₂) | 200° |
| 134 | CN | —CO—C₆H₃Cl₂(3,5) | 183° |
| 135 | CN | —CO—C₆H₄—CH₃(2) | 182° |
| 136 | CN | —CO—C₆H₄—OCH₃(2) | 166° |
| 137 | CN | —CH₂—C₆H₅ | 125° |
| 138 | Cl | H | >180° (decomposition) |
| 139 | Cl | —CONH—C₆H₅ | 167° (decomposition) |
| 140 | Cl | —CONH—CH₃ | >130° (decomposition) |
| 141 | Cl | —CONH—C₆H₄Cl(4) | 188–193° |
| 142 | CN | —CO—NH—CH₂—CH=CH₂ | 150° (decomposition) |
| 143 | H | H | 167° | and also the following compounds of the formula $$\underset{N}{\text{pyridine}}\text{ with } R_{17}, R_{18}, R_{19}$$

| Compound No. | $R_{17}$ | $R_{18}$ | $R_{19}$ | Salt | Melting point |
|---|---|---|---|---|---|
| 144 | 2-CH=NOH | 3-OH | 6-CH₃ | — | (solid) |
| 145 | 4-CH=NOCONHCH₃ | 2-Cl | 6-Cl | — | 156° |
| 146 | 4-CH=NOH | 2-Cl | 6-Cl | — | 183° |
| 147 | 3-CH=NOH | 2-Cl | 6-Cl | — | 219° |
| 148 | 4-CH=NO—CO—(furyl) | 2-Cl | 6-Cl | — | 156° |
| 149 | 4-CH=NO—CO—NH—C₆H₃(Cl)(CF₃) | H | H | — | 166° |
| 150 | 2-C(CH₃)=NO—COSC₆H₅ | H | H | — | 78° |
| 151 | 4-C(Cl)=NOH | H | H | HCl | >190° (decomposition) |
| 152 | 2-C(CH₃)=NO—CONHCH₃ | H | H | — | 132° |
| 153 | 4-C(nC₁₁H₂₃)=NO—CONHCH₃ | H | H | — | 69° |
| 154 | 4-C(COOC₄H₉n)=NOH | H | H | — | 186° |
| 155 | 2-C(CH₃)=NOH | H | H | — | 122° |
| 156 | 2-C(CH₃)=NO—COSC₂H₅ | H | H | — | (oil) |
| 157 | 4-C(CH₃)=NO—COSC₂H₅ | H | H | — | (oil) |
| 158 | 4-C(nC₁₀H₂₃)=NOH | H | H | — | 103° |
| 159 | 3-C(CH₃)=NOH | H | H | — | 115° |
| 160 | 4-C(CN)=NOH | H | H | — | 284° |
| 161 | 2-CH=NOCH₂CN | H | H | — | (oil) |
| 162 | 2-CH=NOCH₂CH₂Cl | H | H | — | (oil) |
| 163 | 4-CH=NOCH₂CH₂Cl | H | H | — | (oil) | and also the compound

No. 164  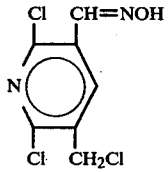  Melting point 184° and also compounds of the formula

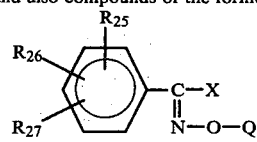

-continued

| Compound No. | X | $R_{25}$ | $R_{26}$ | $R_{27}$ | Q | Melting point |
|---|---|---|---|---|---|---|
| 165 | $C_2H_5$ | 2-OCONHCH$_3$ | 4-CH$_3$ | H | —CONHCH$_3$ | 131° |
| 166 | nC$_3$H$_7$ | 2-OCONHCH$_3$ | 4-Cl | 5-Cl | —CONHCH$_3$ | 133° |
| 167 | CH$_3$ | 2-OCOCH$_3$ | 4-Cl | 6-Cl | H | 156° |
| 168 | C$_2$H$_5$ | 2-OCOCH$_3$ | 4-Cl | 6-Cl | H | 145° |
| 169 | CH$_3$ | H | n-C$_{10}$H$_{21}$O | H | H | 79° |
| 170 | CH$_3$ | 4-C$_6$H$_4$F(p) | H | H | H | 149° |
| 171 | CH$_3$ | 4-C$_6$H$_5$ | H | H | H | 189° |
| 172 | CH$_3$ | 4-C$_6$H$_5$—CH$_2$O— | H | H | H | 206° |
| 173 | CH$_3$ | 4-Cyclohexyl | H | H | H | 118° |
| 174 | CH$_3$ | 4-C$_6$H$_5$(CH$_2$)$_3$O— | H | H | H | 113° |
| 175 | CH$_3$ | 2-C$_6$H$_5$—CH$_2$O— | H | H | H | 114° |
| 176 | CH$_3$ | 4-C$_6$H$_4$Br(p) | H | H | H | 215–219° |
| 177 | CH$_3$ | 2-OH | 4-Cl | 6-Cl | H | 133° |
| 178 | C$_2$H$_5$ | 2-OH | 4-Cl | 6-Cl | H | 98° |
| 179 | nC$_3$H$_7$ | 2-OH | 4-Cl | 6-Cl | H | 155° |
| 180 | C$_2$H$_5$ | 2-OH | 4-Cl | 6-Cl | H | 83° |
| 181 | C$_2$H$_5$ | 4-OH | 3-CH$_3$ | 5-CH$_3$ | H | 148–154° |
| 182 | nC$_3$H$_7$ | 2-OH | 4-Cl | 5-Cl | H | 121° |
| 183 | C$_2$H$_5$ | 2-OH | 4-CH$_3$ | H | H | 105° |
| 184 | CH$_3$ | 2-OH | H | 5-Cl | H | 169° |
| 185 | C$_2$H$_5$ | 2-OH | H | 5-CH$_3$ | H | 140° |
| 186 | CH$_3$ | 2-OH | H | 5-Cl | CH$_2$CN | 98° | and also the following compounds of the formula

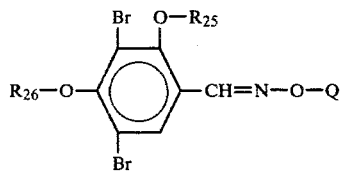

| Compound No. | $R_{25}$ | $R_{26}$ | Q | Melting point |
|---|---|---|---|---|
| 187 | —CONHC$_2$H$_5$ | —CONHC$_2$H$_5$ | —CONHC$_2$H$_5$ | 138° |
| 188 | —CONHC$_6$H$_5$ | —CONHC$_6$H$_5$ | —CONHC$_6$H$_5$ | (solid) |
| 189 | —CONHC$_4$H$_9$(n) | —CONHC$_4$H$_9$(n) | —CONHC$_4$H$_9$(n) | 152–160° |
| 190 | —CONH—⟨H⟩ | —CONH—⟨H⟩ | —CONH—⟨H⟩ | |
| 191 | —CONH—CH$_3$ | —CH$_2$—CH=CH$_2$ | —CONHCH$_3$ | |
| 192 | —CONHC$_2$H$_5$ | —CH$_2$—CH=CH$_2$ | —CONHC$_2$H$_5$ | |
| 193 | —CONHC$_6$H$_5$ | —CH$_2$—CH=CH$_2$ | —CONHC$_6$H$_5$ | |
| 194 | —CONHCH$_3$ | —CH$_3$—C≡CH | —CONHCH$_3$ | |
| 195 | —CONHC$_2$H$_5$ | —CH$_2$—C≡CH | —CONHC$_2$H$_5$ | |
| 196 | —CONHC$_6$H$_5$ | —CH$_2$—C≡CH | —CONHC$_6$H$_5$ | |
| 197 | —CH$_3$ | —CH$_3$ | —COCH$_2$Cl | 101–103° |
| 198 | —CONHCH$_3$ | —CONHCH$_3$ | —CONHCH$_3$ | 133° | and also the following compounds of the formula

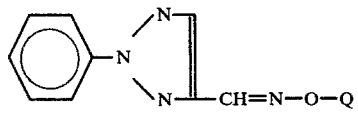

| Compound No. | Q | Melting point |
|---|---|---|
| 199 | H | 135–136° |
| 200 | —CONHCH$_3$ | 130° |
| 201 | —CONH—C$_3$H$_7$(n) | 118° |
| 202 | —CONH—CH$_2$CH$_2$—Cl | 167–171° |
| 203 | —CON(CH$_3$)$_2$ | 120–128° | and also the following compounds of the formula

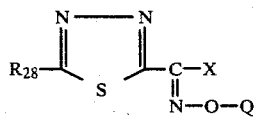

Compound                                                           Melting

-continued

| No. | X | $R_{28}$ | Q | point |
|---|---|---|---|---|
| 204 | CN | $CH_3-S-$ | H | >200° (decomposition) |
| 205 | CN | $C_2H_5-O-$ | H | 193° (decomposition) |
| 206 | CN | $CH_3-S-$ | $-CH_2-CN$ | 111° |
| 207 | CN | $CH_3-S-$ | $-CH(CH_3)COOCH_3$ | 96° |
| 208 | CN | $C_2H_5-O-$ | $-CH_2-CN$ | (semi-solid) |
| 209 | CN | $C_2H_5-O-$ | $-CH(CH_3)COOCH_3$ | 58-63° |
| 210 | Cl | $C_6H_5$ | H | 222° (decomposition) |
| 211 | Cl | $CH_3-S-$ | H | 187° |
| 212 | Cl | $CH_3-SO_2$ | H | 187° (decomposition) |
| 213 | $-COOC_2H_5$ | $CH_3O-$ | H | 151-156° |
| 214 | $-COOC_2H_5$ | $CH_3S-$ | H | 130° (decomposition) |
| 215 | $-COOC_2H_5$ | $CH_3SO-$ | H | 134° |
| 216 | $-COOCH_3$ | $CH_3S-$ | H | (decomposition) |
| 216a | $-COOCH_3$ | $CH_3SO$ | H | 138° (decomposition) | and also the following compounds of the formula

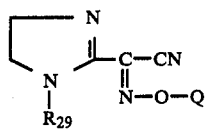

| Compound No. | $R_{29}$ | Q | Melting point |
|---|---|---|---|
| 217 | $CH_3$ | H | 216.5° |
| 218 | H | H | >250° (decomposition) |
| 219 | $CH_3$ | $-CONHCH_3$ | 186-190° (decomposition) |
| 220 | $CH_3$ | 2-Furanoyl | 153-157° (decomposition) |
| 221 | $CH_3$ | $-CH_2CN$ | 94-96° |
| 222 | $CH_3$ | $-CH(CH_3)COOCH_3$ | (oil) |
| 223 | $CH_3$ | $-CH_2-CH=CH_2$ | |
| 224 | $CH_3$ | $-CH_2-CH=CH-CH_3$ | |
| 225 | $CH_3$ | $-CH_2-C\equiv CH$ | |
| 226 | $CH_3$ | $-CH_2-CONH_2$ | | and also the following compounds of the formula

| Compound No. | $R_{30}$ | $R_{31}$ | Melting point |
|---|---|---|---|
| 227 | H | $-CH=CH-\underset{NOH}{\overset{\|}{C}}-COOH$ | 165° (decomposition) |
| 228 | H | $-CH=CH-\underset{N-O-C_2H_5}{\overset{\|}{C}}-COOH$ | 68-82° |
| 229 | $-C_6H_3Cl_2(2,4)$ | $-CH=NOH$ | 163° |
| 230 | $-C_6H_3Cl_2(2,4)$ | $-CH=NO-C(CH_3)COOCH_3$ | 59-65° |
| 231 | $-C_6H_4Cl(4)$ | $-CH=NOH$ | 140° |
| 232 | $-C_6H_4Cl(4)$ | $-CH=NO-C(CH_3)COOCH_3$ | (semi-solid) | and also the following compounds of the formula

-continued

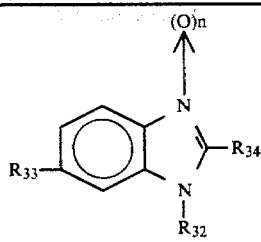

| Compound No. | n | $R_{32}$ | $R_{33}$ | $R_{34}$ | Melting point |
|---|---|---|---|---|---|
| 233 | 1 | —CH$_3$ | H | —CH=NOH | 228° (decomposition) |
| 234 | 1 | —CH$_3$ | Cl | —CH=NOH | 145-7° |
| 235 | 1 | —C$_6$H$_5$ | H | —CH=NOH | 208-209° |
| 236 | 0 | —COOCH$_3$ | H | —C(Cl)=NOH | 166° (decomposition) | and also the following compounds of the formula

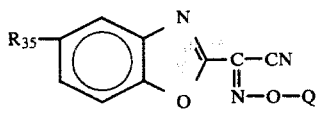

| Compound No. | $R_{35}$ | Q | Melting point |
|---|---|---|---|
| 237 | tert.C$_4$H$_9$ | H | 101-105° |
| 238 | tert.C$_4$H$_9$ | —CON(CH$_3$)$_2$ | 190° |
| 239 | CH$_3$ | H | 204° |
| 240 | CH$_3$ | —CON(CH$_3$)$_2$ | 194° |
| 241 | Cl | H | 208° |
| 242 | Cl | —CON(CH$_3$)$_2$ | 177° |
| 243 | CH$_3$ | —CH$_2$—CN | |
| 244 | CH$_3$ | —CH$_2$—CH=CH—CH$_3$ | | and also the following compounds of the formula

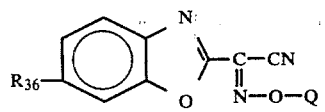

| Compound No. | $R_{36}$ | Q | Melting point |
|---|---|---|---|
| 245 | CH$_3$ | H | 223° |
| 246 | CH$_3$ | —CON(CH$_3$)$_2$ | 211° |
| 247 | NO$_2$ | H | 122-124° (decomposition) |
| 248 | NO$_2$ | —CON(CH$_3$)$_2$ | about 180° |
| 249 | CH$_3$ | —CH$_2$CN | solid |
| 250 | CH$_3$ | —CH$_2$—CH=CH$_2$ | solid |
| 251 | CH$_3$ | —CH$_2$—C≡CH | solid | and also the following compounds

No. 252 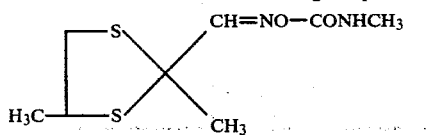 melting point 100°

No. 253 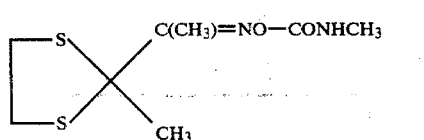 melting point 107°

No. 254 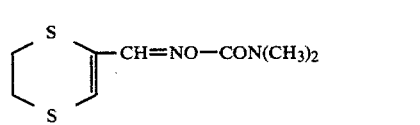 solid

-continued

No. 255

[structure: dithiane ring with -CH=NO-CONHC₂H₅]

Melting point 122°

[structure with O=, H₅C₂—N, N—CH₃, C=S, CH=N—O—Q]

| No. | | Melting point |
|---|---|---|
| No. 256 | Q = H | Melting point 108° |
| No. 257 | Q = —CONHCH₃ | Melting point 185° |
| No. 258 | Q = —CON(CH₃)₂ | Melting point 95° |

No. 259

[structure with OH, CH₃, C=NOH, H₃C, O, =O]

Melting point 138–141°

No. 260

[structure with OH, CH₃, C=NOH, H₃C, N-H, =O]

Melting point 203–205°

No. 261

[structure with H, N, O=C, CH₃, C=NOH, N, H, O]

Melting point 235°

No. 262

[structure with H₃CO, OCH₃, O, CH=NO—CONHCH₃]

Boiling point 90–130°

No. 263

[structure with H₃C, O, CH₃, CH=NO—CONHCH₃]

Melting point 99–105° and also the following compounds of the formula

[structure: HO, isoC₃H₇, N-R₃₇, =O, CH₃, C=NO—Q]

| Compound No. | R₃₇ | Q | Physical constant |
|---|---|---|---|
| 264 | H | C₂H₅ | oil |
| 265 | —CH₂—C₆H₅ | C₂H₅ | oil |
| 266 | —CH₂—C₆H₄Cl(2) | C₂H₅ | oil |
| 267 | —CH₂—C₆H₅ | C₄H₉(n) | oil |
| 268 | —CH₂—C₆H₄Cl(2) | C₄H₉(n) | oil | and also the following compounds of the formula

[structure: R₃₈, R₃₉, S, C-X, NOH]

Compound                                                    Physical

-continued

| No. | $R_{38}$ | $R_{39}$ | X | constant |
|---|---|---|---|---|
| 269 | H | H | CN | |
| 270 | Br | H | CN | oil |
| 271 | Br | H | $CH_3$ | oil |
| 272 | H | H | $CH_3$ | melting point 93–108° |
| 273 | H | Cl | $CH_3$ | |
| 274 | H | Cl | $-COOCH_3$ | |
| 275 | H | Cl | $-COOCH_3$ | |
| 276 | H | Cl | $-CON(CH_3)_2$ | |
| 277 | H | Cl | Cl | |
| 278 | Br | H | Cl | oil |
| 279 | Cl | Cl | Cl | oil | and also the compounds

No. 280 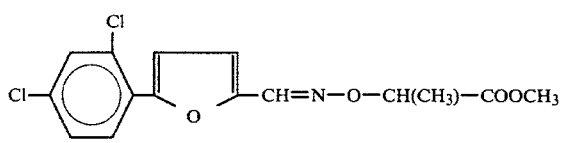   melting point 59–65°

No. 281 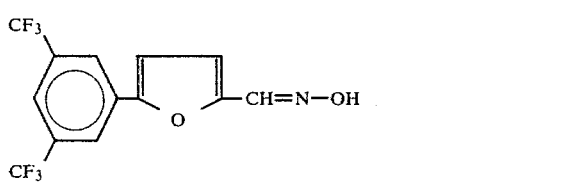   solid

No. 282 

As already mentioned, various methods and techniques are possible for the use of the compounds of the formula I for protecting cultivated plants against agricultural chemicals:

(1.) Seed dressing (a) Dressing of the seeds with an active substance formulated as a wettable powder, by shaking in a vessel until the formulation is uniformly distributed on the surface of the seed (dry dressing). About 10 to 500 g of the active substance of the formula I (40 g to 2 kg of wettable powder) are used per 100 kg of seed.

(b) Dressing of the seeds with an emulsion concentrate of the active substance of the formula I according to method (a) (wet dressing).

(c) Dressing by immersing the seed in a liquor containing 50–3,200 ppm of the active substance of the formula I for 1–72 hours and, if desired, subsequently drying the seed (immersion dressing).

Dressing of the seed or treatment of the germinated young seedling are, of course, the preferred methods of application, because the treatment with the active substance is directed entirely towards the intended crop. As a rule 10 g to 500 g and preferably 50 to 250 g of active substance are used per 100 kg of seed and, depending on the method, which also enables other active substances or micronutrients to be added, it is possible to use concentrations in excess of or below the indicated limiting concentrations (repeat dressings).

(2) Application from a tank mixture

A liquid formulation of a mixture of antidote and herbicide (reciprocal ratio between 1:20 and 5:1) is used and the amount of herbicide applied is 0.1 to 6 kg per hectare. A tank mixture of this type is preferably applied before or immediately after sowing or is worked into the as yet unsown soil to a depth of 5–10 cm.

(3) Application into the seed furrow

The antidote is introduced, in the form of an emulsion concentrate or wettable powder or as granules, into the open sown seed furrow and, after convering the seed furrow in the normal way, the herbicide is then applied by the pre-emergence process.

Thus, in principle, the antidote can be applied before, together with or after the pesticide and can be used on the seed or on the field before or after sowing or in certain cases also after germination of the seed.

(4) Controlled release of the active substance

The active substance is absorbed, as a solution, on mineral granule carriers or polymerised granules (urea/formaldehyde) and allowed to dry. If desired, a coating can be applied (coated granules) which enables the active substance to be released in a metered manner over a specific period.

Of course, all other methods for application of active substances can also be employed. Examples of these are given below.

The compounds of the formula I can be used on their own or together with suitable carriers and/or other additives. Suitable carriers and additives can be solid or liquid and correspond to the substances commonly used in formulation technology, for example natural or regenerated mineral substances, solvents, dispersing agents, wetting agents, adhesives, thickeners, binders or fertilisers.

The content of active substance in marketable agents is between 0.1 and 90%.

For application, the compounds of the formula I can be in the following processing forms (the percentages by weight in brackets representing advantageous amounts of active substance): Solid processing forms: dusts and sprinkling agents (up to 10%), granules, coated granules, impregnated granules and homogeneous granules and pellets (grains) (1 to 80%);

Liquid processing forms:

(a) active substance concentrates which are dispersible in water: wettable powders and pastes (25–90% in commercial packs and 0.01 to 15% in ready-to-use solutions); and emulsions concentrates and solution concentrates (10 to 50%; 0.01 to 15% in ready-to-use solutions);

(b) solutions (0.1 to 20%) and aerosols.

The active substances of the formula I of the present invention can be formulated, for example, as follows:

Dusts:

The following substances are used to formulate (a) 5% and (b) a 2% dust:

(a)
 5 parts of active substance
 95 parts of talc;

(b)
 2 parts of active substance
 1 part of highly dispersed silicic acid
 97 parts of talc.

The active substances are mixed with the carriers and ground and in this form can be processed to dusts for application.

Granulate:

The following substances are used to formulate a 5% granulate:
5 parts of active substance
0.25 part of epichlorohydrin
0.25 part of cetyl polyglycol ether
3.50 parts of polyethylene glycol
91 parts of kaolin (particle size 0.3–0.8 mm).

The active substance is mixed with epichlorohydrin and the mixture is dissolved in 6 parts of acetone. Then polyethylene glycol and cetyl polyglycol ether are added. The resultant solution is sprayed on kaolin and the acetone is then evaporated in vacuo. A microgranulate of this type can advantageously be worked into seed furrows.

Wettable powders:

The following constituents are used to formulate (a) a 70%, (b) a 40%, (c) and (d) a 25% and (e) a 10% wettable powder:

(a)
 70 parts of active substance
 5 parts of sodium dibutylnaphthylsulfonate
 3 parts of naphthalenesulfonic acid/phenolsulfonic acid/formaldehyde condensate (3:2:1)
 10 parts of kaolin
 12 parts of Champagne chalk (b)
 40 parts of active substance
 5 parts of sodium ligninsulfonate
 1 part of sodium dibutylnaphthalenesulfonate
 54 parts of silicic acid (c)
 25 parts of active substance
 4.5 parts of calcium ligninsulfonate
 1.9 parts of Champagne chalk/hydroxyethylcellulose mixture (1:1)
 1.5 parts of sodium dibutylnaphthalenesulfonate
 19.5 parts of silicic acid
 19.5 parts of Champagne chalk
 28.1 parts of kaolin (d)
 25 parts of active substance
 2.5 parts of isooctylphenoxy-polyoxyethyleneethanol
 1.7 parts of a Champagne chalk/hydroxyethylcellulose mixture (1:1)
 8.3 parts of sodium aluminium silicate
 16.5 parts of kieselguhr
 46 parts of kaolin (e)
 10 parts of active substance
 3 parts of a mixture of the sodium salts of saturated fatty alcohol sulfates
 5 parts of naphthalenesulfonic acid/formaldehyde condensate
 82 parts of kaolin.

The active substances are intimately mixed in suitable mixers with the additives and ground in appropriate mills and rollers. Wettable powders of excellent wettability and suspension power are obtained. These wettable powders can be diluted with water to give suspensions of the desired concentration and can be used in particular for dressing seeds and for the immersion treatment of cuttings.

Emulsifiable concentrate:

The following substances are used to formulate a 25% emulsifiable concentrate:
25 parts of active substance
2.5 parts of epoxidised vegetable oil
10 parts of an alkylarylsulfonate/fatty alcohol polyglycol ether mixture
5 parts of dimethylformamide
57.5 parts of xylene.

By diluting such a concentrate with water it is possible to prepare emulsions of any desired concentration, which are especially suitable for dressing seeds and for the immersion treatment of young plants.

Pre-emergence antidote test (basic test)

General test method:

Small flower pots (diameter 6 cm at the top) are filled with garden soil into which the plant seed is sown, covered with the soil and gently pressed firm. The substance to be tested as an antidote is then sprayed in the form of a dilute solution (obtained from a wettable powder) in an amount corresponding to 4 kg of active substance/ha. The herbicide is sprayed onto the soil directly afterwards in corresponding amount. After the pots have stood for 18 days at about 20°–23° C. and 60–70% relative atmospheric humidity, evaluation is made in accordance with a linear scale from 1 to 9, 1 denoting total damage to the plant and 9 denoting undamaged healthy plant. Plants without antidote protection are used as control.

The following herbicides and plants were employed:
(1) 1.5 kg/ha of the active substance α-[4-(p-trifluoromethylphenoxy)-phenoxy]-propionic acid n-butoxyethyl ester in maize of the "Orla 264" variety.

(2) 1.5 kg/ha of the active substance Metolachlor=N-(1-methyl-2-methoxyethyl)-N-chloroacetyl-2-ethyl-6-methylaniline in sorghum of the "Funk G-522" variety.

(3) 2 kg/ha of the active substance Prometryn=2,4-bis(isopropylamino)-6-methylthio-s-triazine in soybeans.

(4) 2 kg/ha of the active substance 4-ethylamino-6-tert.-butylamino-2-chloro-s-triazine in wheat of the "Farnese" variety.

(5) 4 kg/ha of the active substance Prometryn=2,4-bis(isopropylamino)-6-methylthio-s-triazine in sorghum of the "Funk G-522" variety.

(6) 2 kg/ha of the active substance α-[4-(p-trifluoromethylphenoxy)-phenoxy]-propionic acid n-butoxyethyl ester in barley of the "Mazurka" variety.

Compounds of the formula I give a good antidote action in these tests. The following results are given by way of example.

| Test variant | Compound No. | Rating of the herbicidal influence (without/with antidote) |
|---|---|---|
| 4 | 280 | 2/5 |
| 5 | 234 | 6/8 |
| 6 | 209 | 6/8 |
| 6 | 163 | 4/6 |
| 6 | 272 | 3/8 |
| 5 | 175 | 3/6 |
| 5 | 174 | 3/5 |
| 5 | 87a | 3/6 |
| 5 | 101 | 1/6 |
| 5 | 199 | 1/6 |
| 5 | 234 | 6/8 |
| 2 | 198 | 2/8 |
| 3 | 16 | 3/5 |
| 4 | 29a | 2/7 |
| 2 | 281 | 3/5 |
| 4 | 281 | 2/4 |
| 5 | 824 | 2/6 |
| 5 | 124a | 1/5 |

Antidote action on separate application (antidote/pre-emergence, herbicide/post-emergence)

General test method:

Small flower pots (diameter 6 cm at the top) are filled with sandy loam soil into which the plant seed is sown. After covering the seed, the substance to be tested as an antidote is sprayed onto the surface, in the form of a dilute solution and in an amount which, when converted, corresponds to 4 kg of active substance/ha. The pots are kept at 20°–23° C. and 60–70% relative atmospheric humidity. When the plants have reached the 2- to 3-leaf stage after 10 days, they are treated, as indicated below, with the corresponding amount of herbicide. 14 days after application of the herbicide, evaluation is made in accordance with a linear scale from 1 to 9, 1 denoting total damage to the plant and 9 denoting undamaged healthy plant. Plants without antidote protection are used as control.

The herbicides and plants used are:

(1) 4.0 kg/ha of the active substance Ametryn=2-ethylamino-4-isopropylamino-6-methylthio-s-triazine in maize of the "Orla 264" variety.

(2) 1.0 kg/ha of the active substance Prometryn=2,4-bis-(isopropylamino)-6-methylthio-s-triazine in sorghum of the "Funk G-522" variety.

(3) 0.25 kg/ha of the active substance α-[4-(p-trifluoromethylphenoxy)-phenoxy]-propionic acid n-butoxyethyl ester in barley of the "Mazurka" variety.

Compounds of the formula I showed a good antidote action in these tests.

Antiodote action in transplanted rice on separate application (antidote/pre-emergence, herbicide/post-emergence)

Plastic tubs (8×8 cm, 10 cm high) are filled with wet marshy soil to 2 cm below the edge. The substance to be tested as an antidote is sprayed, as a dilute solution, onto the surface of the soil in an amount corresponding to 4 kg of active substance/ha. Rice plants of the "IR-88" variety are transplanted in the 1½- to 2-leaf stage into the prepared tubs. On the next day, the water level is raised to about 1.5 cm. Four days after transplantation, 2-ethylamino-4-(1,2-dimethyl-n-propylamino)-6-methylthio-s-triazine is added to the water in granule form in an amount which, when converted, corresponds to 0.75 kg of active substance/ha. During the test period, the temperature is 26°–28° C. and the relative atmospheric humidity 60–80%. 20 days after the treatment with herbicide, evaluation is made in accordance with a linear scale from 1 to 9, 1 denoting total damage to the plant and 9 denoting undamaged healthy plant. Plants not protected with antidote are used as control.

Good antidote results were obtained with the compounds of the formula I. The following results are given by way of example.

| Compound No. | Rating of the herbicidal influence (without/with antidote) |
|---|---|
| 245 | 5/7 |
| 235 | 3/8 |
| 259 | 5/8 |
| 234 | 3/5 |
| 16 | 2/6 |
| 272 | 3/5 |
| 65 | 4/7 |
| 87a | 4/6 |
| 184 | 5/7 |
| 128 | 5/7 |
| 77 | 5/8 |
| 94 | 5/7 |
| 228 | 4/7 |

Pre-emergence antidote test in nutrient solution

A Hewitt nutrient solution, which contains the amount of herbicide indicated below as well as 10 ppm of the antidote to be tested, is prepared.

Seeds which would normally be expected to be damaged in the indicated test concentrations of the herbicide employed are used and sown in granular zonolith (expanded vermiculite) in a plastic flower pot (diameter 6 cm at the top) which is perforated at the bottom. This pot is then placed in a second transparent plastic flower pot (diameter 7 cm at the top) which contains about 50 ml of the nutrient solution prepared with herbicide and antidote. This nutrient solution then rises by capillary action in the filling material of the smaller pot and moistens the seed and the germinating plant. The loss in fluid is daily replenished to 50 ml with pure Hewitt nutrient solution. 3 weeks after the start of the test, evaluation is made in accordance with a linear scale from 1 to 9, 1 denoting total damage to the plant and 9 denoting undamaged healthy plant. The control solution employed in the parallel test contains no added antidote.

The herbicides and plants employed are:

(1) 4 ppm of Prometryn=2,4-bis(isopropylamino)-6-methylthio-s-triazine in sorghum of the "Funk G-522" variety.

(2) 4 ppm of 4-ethylamino-6-tert.-butylamino-2-chloro-s-triazine in wheat of the "Farnese" variety.

(3) 4 ppm of α-[4-(p-trifluoromethylphenoxy)-phenoxy]-propionic acid n-butoxyethyl ester in barley of the "Mazurka" variety.

(4) 5 ppm of Metolachlor=N-(1-methyl-2-methoxyethyl)-N-chloroacetyl-2-ethyl-6-methylaniline in sorghum of the "Funk G-522" variety.

A good antidote action is obtained with the compounds of the formula I. The following results are given by way of example:

| Test variant | Compound No. | Rating of the herbicidal influence (without/with antidote) |
|---|---|---|
| 4 | 227 | 4/6 |
| 1 | 151 | 2/4 |
| 1 | 269 | 2/6 |
| 1 | 198 | 1/7 |
| 2 | 198 | 1/4 |
| 2 | 282 | 2/6 |
| 4 | 211 | 5/8 |
| 1 | 170 | 2/5 |
| 1 | 174 | 2/4 |
| 1 | 109 | 2/5 |
| 3 | 111 | 2/7 |
| 3 | 114 | 5/8 |
| 3 | 110 | 5/7 |
| 4 | 259 | 2/4 |
| 2 | 197 | 1/3 |

Pre-emergence antidote test in nutrient solution (rice).

A Hewitt nutrient solution is prepared which additionally contains 10 ppm of the antidote to be tested.

Rice seed of the "IR-8" variety is sown in inert filling material (granular zonolith) in a plastic flower pot (diameter 6 cm at the top) which is perforated at the bottom. This pot is placed in a second transparent plastic flower pot (diameter 7 cm at the top) which contains about 50 ml of the prepared nutrient solution; this nutrient solution then rises by capillary action in the filling material of the smaller pot and moistens the seed and the germinating plant. The loss in fluid is daily replenished to 50 ml with pure Hewitt nutrient solution. After 15 days the rice plants are transplanted in the 2- to 2½-leaf stage into rectangular plastic tubs (8×8 cm, 10 cm high) which are filled with 500 ml of wet marshy soil. On the next day the water level in these tubs is raised to 1–2 cm above the base level. 4 days after transplantation, the herbicide 2-ethylamino-4-(1,2-dimethyl-n-propylamino)-6-methylthio-s-triazine is added in granule form and in an amount which, when converted, corresponds to 0.75 kg of active substance/ha. 3 weeks after adding the herbicide, evaluation is made in accordance with a linear scale from 1 to 9, 1 denoting total damage to the plant and 9 denoting undamaged healthy plant. The control solution employed in the parallel test contains no added antidote. Compounds of the formula I showed an antidote action in this test.

Post-emergence antidote test in nutrient solution

General test method:

Small plastic flower pots (diameter 6 cm at the top), which are perforated at the bottom, are filled with granular zonolith and the seeds are sown in this material. The pot is then placed in a second transparent plastic flower pot (diameter 7 cm at the top) which contains 50 ml of water which rises by capillary action and moistens the seed. From the 5th day, the continual loss in water is made up with Hewitt nutrient solution. From the 15th day, when the plant is in the 1½- to 2-leaf stage, 10 ppm of the antidote to be tested and the amount of herbicide indicated below are added to the nutrient solution which has again been replenished to 50 ml. From the 16th day, the loss in fluid is again made up with pure Hewitt nutrient solution. During the entire duration of the test, the temperature is 20°–23° C. and the relative atmospheric humidity 60–70%.

3 weeks after the addition of the herbicide and of the antidote, evaluation is made in accordance with a linear scale from 1 to 9, 1 denoting total damage to the plant and 9 denoting undamaged healthy plant.

Test variants:

(1) 15 ppm of α-[4-(3,5-dichloropyridyl-2-oxy)-phenoxy]-propionic acid propargylthiolo-ester in wheat of the "Zenith" variety.

(2) 4 ppm of 4-ethylamino-6-tert.-butylamino-2-chloro-s-triazine in wheat of the "Zenith" variety.

(3) 2 ppm of α-[4-(p-trifluoromethylphenoxy)-phenoxy]-propionic acid n-butoxyethyl ester in maize of the "Orla" variety.

(4) 8 ppm of α-[4-(p-trifluoromethylphenoxy)-phenoxy]-propionic acid n-butoxyethyl ester in sorghum of the "Funk G-522" variety.

(5) 4 ppm of Prometryn=2,4-bis(isopropylamino)-6-methylthio-s-triazine in sorghum of the "Funk G-522" variety.

(6) 8 ppm of α-[4-(3,5-dichloropyridyl-2-oxy)phenoxy]-propionic acid methyl ester in wheat of the "Zenith" variety.

Compounds of the formula I give a good antidote action in these tests. The following results are given by way of example:

| Test variant | Compound No. | Rating of the herbicidal influence (without/with antidote) |
|---|---|---|
| 5 | 170 | 1/3 |
| 1 | 209 | 3/5 |
| 5 | 71 | 2/4 |
| 1 | 160 | 3/6 |
| 1 | 242 | 3/7 |
| 1 | 222 | 6/8 |
| 5 | 151 | 1/4 |
| 1 | 207 | 6/8 |

Antidote test–seed soaking

Rice seeds of the IR-8 variety are immersed for 48 hours in solutions of the test substances in concentrations of 10 or 100 ppm. The seeds are then allowed to dry for about 2 hours until they are no longer tacky. Rectangular plastic tubs (8×8 cm, 10 cm high) are filled with sandy loam to 2 cm below the edge. 4 g of seeds are sown in each tub and only very loosely covered (to about the diameter of the seed). The soil is kept in a moist (non-marshy) state. The herbicide N-(1-methyl-2-methoxyethyl)-N-chloroacetyl-2-ethyl-6-methylaniline or N-propoxyethyl-N-chloroacetyl-2,6-diethylaniline, as desired, is then applied as a dilute solution and in an amount which, when converted, corresponds to 1.5 kg of active substance/ha. 18 days after transplantation, evaluation is made in accordance with a linear scale from 1 to 9, 1 denoting total damage to the plant and 9 denoting undamaged healthy plant.

Compounds of the formula I show a good antidote action in this test. The following results are given by way of example.

|  | Compound No. | Rating of the herbicidal influence (without/with antidote) |
| --- | --- | --- |
| 100 ppm | 8a | 3/6 |
| 10 ppm | 8a | 3/6 |
| 10 ppm | 7 | 3/6 |
| 10 ppm | 281 | 2/6 |
| 10 ppm | 282 | 3/5 |
| 10 ppm | 23 | 4/6 |
| 10 ppm | 151 | 2/6 |
| 10 ppm | 257 | 4/6 |
| 10 ppm | 174 | 2/4 |
| 10 ppm | 66 | 2/4 |
| 10 ppm | 109 | 2/5 |
| 100 ppm | 111 | 2/4 |
| 10 ppm | 113 | 3/7 |
| 100 ppm | 113 | 3/6 |
| 100 ppm | 53 | 3/7 |
| 10 ppm | 53 | 3/5 |
| 10 ppm | 93 | 3/6 |
| 10 ppm | 110a | 3/6 |
| 10 ppm | 84a | 3/6 |
| 10 ppm | 199 | 2/6 |
| 100 ppm | 95 | 3/6 |
| 100 ppm | 97 | 3/6 |
| 100 ppm | 99 | 3/7 |
| 100 ppm | 186 | 2/6 |
| 10 ppm | 220 | 3/6 |

What is claimed is:

1. A compound of the formula

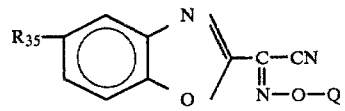

wherein $R_{35}$ is methyl, tert.butyl or chloro, and Q is hydrogen, cyanomethyl, methallyl or $-CON(CH_3)_2$.

2. The compound according to claim 1 in which $R_{35}$ is chloro and Q is $-CON(CH_3)_2$.

3. A compound of the formula

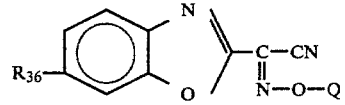

wherein $R_{36}$ is methyl or nitro, and Q is hydrogen, cyanomethyl, allyl, propargyl or $-CON(CH_3)_2$.

4. A compound of the formula

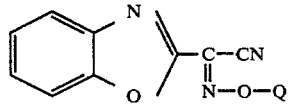

wherein Q is hydrogen; methyl; cyanomethyl; propargyl; benzyl; alkylcarbonyl in which the alkyl group has from 1 to 4 carbon atoms; chloromethylcarbonyl; alkoxycarbonyl in which the alkyl group has from 1 to 4 carbon atoms; ethylthiocarbonyl; alkenylcarbonyl in which the alkenyl group has 2 or 3 carbon atoms; phenylcarbonyl mono-substituted by methyl, methoxy, or nitro, or mono- or di-substituted by chlorine; N-methylcarbamoyl; N-chloromethylcarbamoyl; N-(2'-chloroethyl)-carbamoyl; N-dichlorophenylcarbamoyl; N-allylcarbamoyl; N,N-dimethylcarbamoyl; N-methyl-N-methoxycarbamoyl; 2-furanoyl; or methylsulfonyl.

* * * * *